United States Patent [19]
Yano

[11] Patent Number: 5,557,350
[45] Date of Patent: Sep. 17, 1996

[54] OPHTHALMOMETRIC APPARATUS WITH ALIGNMENT DEVICE INCLUDING FILTER MEANS

[75] Inventor: Nobuyuki Yano, Okazaki, Japan

[73] Assignee: Nidek Co. Ltd., Japan

[21] Appl. No.: 403,662

[22] Filed: Mar. 14, 1995

[30] Foreign Application Priority Data

Apr. 15, 1994 [JP] Japan .................................. 6-102169

[51] Int. Cl.$^6$ .................................. A61B 3/14; A61B 3/10
[52] U.S. Cl. ........................................ 351/208; 351/213
[58] Field of Search .................................. 351/205, 208, 351/213, 221

[56] References Cited

U.S. PATENT DOCUMENTS 5,436,679  7/1995  Ohtsuka et al. ..................... 351/221 X Primary Examiner—William L. Sikes
Assistant Examiner—Huy Mai
Attorney, Agent, or Firm—Rossi & Associates

[57] ABSTRACT

An ophthalmometric apparatus, such as an apparatus for measuring the opacity of the lens of the examinee's eye, comprises an alignment light projecting optical system for projecting alignment light rays on the examinee's eye, a position detecting optical system for detecting the position of a bright spot of corneal reflection formed by the alignment light projecting optical system, a position calculating means for calculating position data representing the position of the examinee's eye relative to a reference position on the basis of detection data provided by the position detecting optical system, an observation optical system for observing the front of the examinee's eye, provided with a filter means for intercepting at least part of the alignment light rays, and a display means for displaying the front of the examinee's eye, the bright spot of the corneal reflection, an image of a reference mark, and position data representing the position of the examinee's eye in an XYZ coordinate system on the observation optical system.

13 Claims, 5 Drawing Sheets

OPHTHALMOMETRIC APPARATUS WITH ALIGNMENT DEVICE INCLUDING FILTER MEANS

BACKGROUND OF THE INVENTION

1. Field of the Invention

The present invention relates to an ophthalmometric apparatus and, more specifically, to an ophthalmometric apparatus for examining and observing a desired part of the examinee's eye through the pupil.

2. Description of the Related Art

An ophthalmometric apparatus aligning method using the bright spot of corneal reflection is used widely for aligning an ophthalmometric apparatus with the examinee's eye in a predetermined positional relationship.

This ophthalmometric apparatus aligning method adjusts the vertical and the horizontal position of an ophthalmometric apparatus relative to the examinee's eye by locating the bright spot in a predetermined positional relation with an image of a reticle on the screen of a TV monitor, and adjusts the axial position of the ophthalmometric apparatus relative to the examinee's eye so that the bright spot is reduced to a minimum size by axially moving the ophthalmometric apparatus; that is, the axial position of the ophthalmometric apparatus is adjusted so that the ophthalmometric apparatus is focused on the bright spot.

Although such a known ophthalmometric apparatus aligning method is effective in setting an ophthalmometric apparatus in a predetermined positional relation to a reference point for alignment in the examinee's eye, the bright spot is blurred when the ophthalmometric apparatus is shifted axially away from the examinee's eye from the position in the predetermined positional relation to the reference point for alignment, for example, when measuring the opacity of the crystalline lens, and the blur of the bright spot is enhanced as the ophthalmometric apparatus is shifted away from the examinee's eye from the position corresponding to the reference point for alignment. Therefore, when measuring a point other than the reference point for alignment, it is difficult to observe the measured point on the screen of the TV monitor because the bright spot is blurred.

SUMMARY OF THE INVENTION

Accordingly, it is an object of the present invention to provide an ophthalmometric apparatus capable of being readily and correctly positioned relative to an objective point in the examinee's eye and of facilitating the observation and the measurement of the objective point.

Another object of the present invention is to provide an ophthalmometric apparatus capable of being repeatedly positioned relative to an objective point in the examinee's eye in high repeatability to facilitate the observation of the process of change of the condition of the objective point in the examinee's eye for the accurate diagnosis of the condition of the objective point in the examinee's eye.

In a first mode of the present invention, an ophthalmometric apparatus having a measuring system to be positioned relative to an objective part in the examinee's eye comprises: an alignment light projecting optical system for projecting alignment light rays on the examinee's eye; a position detecting optical system for detecting the position of a bright spot of corneal reflection formed by the alignment light projecting optical system; a position calculating means for calculating position data representing the position of the examinee's eye relative to the reference position of the ophthalmometric apparatus on the basis of detection data provided by the position detecting optical system; and an observation optical system for observing the front of the examinee's eye, provided with a shading means for intercepting at least part of the alignment light projected by the alignment light projecting optical system and reflected by the cornea.

In a second mode of the present invention, the ophthalmometric apparatus in the first mode of the present invention further comprises a display means for displaying position data representing the position of the examinee's eye, calculated by the position calculating means.

In a third mode of the present invention, the ophthalmometric apparatus in the first mode of the present invention further comprises a storage means for storing the position data calculated by the position calculating means, and a deviation calculating means for reading the position data from the storage means, and comparing the position data read from the storage means and position data representing the existing position of the examinee's eye calculated by the position calculating means to determine the deviation of the existing position from the position represented by the position data read from the storage means.

In a fourth mode of the present invention, the ophthalmometric apparatus in the third mode of the present invention further comprises a display means for displaying the deviation calculated by the deviation calculating means.

In a fifth mode of the present invention, the ophthalmometric apparatus in the third mode of the present invention further comprises a driving means for driving the measuring system for movement according to the deviation calculated by the deviation calculating means.

In a sixth mode of the present invention, the position detecting optical system of the ophthalmometric apparatus in the first mode of the present invention comprises two optical systems for detecting the bright spot of corneal reflection from two different directions respectively.

In a seventh mode of the present invention, the shading means of the ophthalmometric apparatus in the first mode of the present invention has a central region that transmits the alignment light rays therethrough.

In an eighth mode of the present invention, the shading means of the ophthalmometric apparatus in the first mode of the present invention intercepts the alignment light rays completely, and the observation optical system has a display means for displaying the position data representing the position of the examinee's eye calculated by the position calculating means.

BRIEF DESCRIPTION OF THE DRAWINGS

The above and other objects, features and advantages of the present invention will become more apparent from the following description taken in connection with the accompanying drawings, in which.

DETAILED DESCRIPTION OF THE PREFERRED EMBODIMENTS

An ophthalmometric apparatus in a preferred embodiment according to the present invention will be described hereinafter as applied to the measurement of the opacity of the lens of the examinee's eye.

Figure 1:
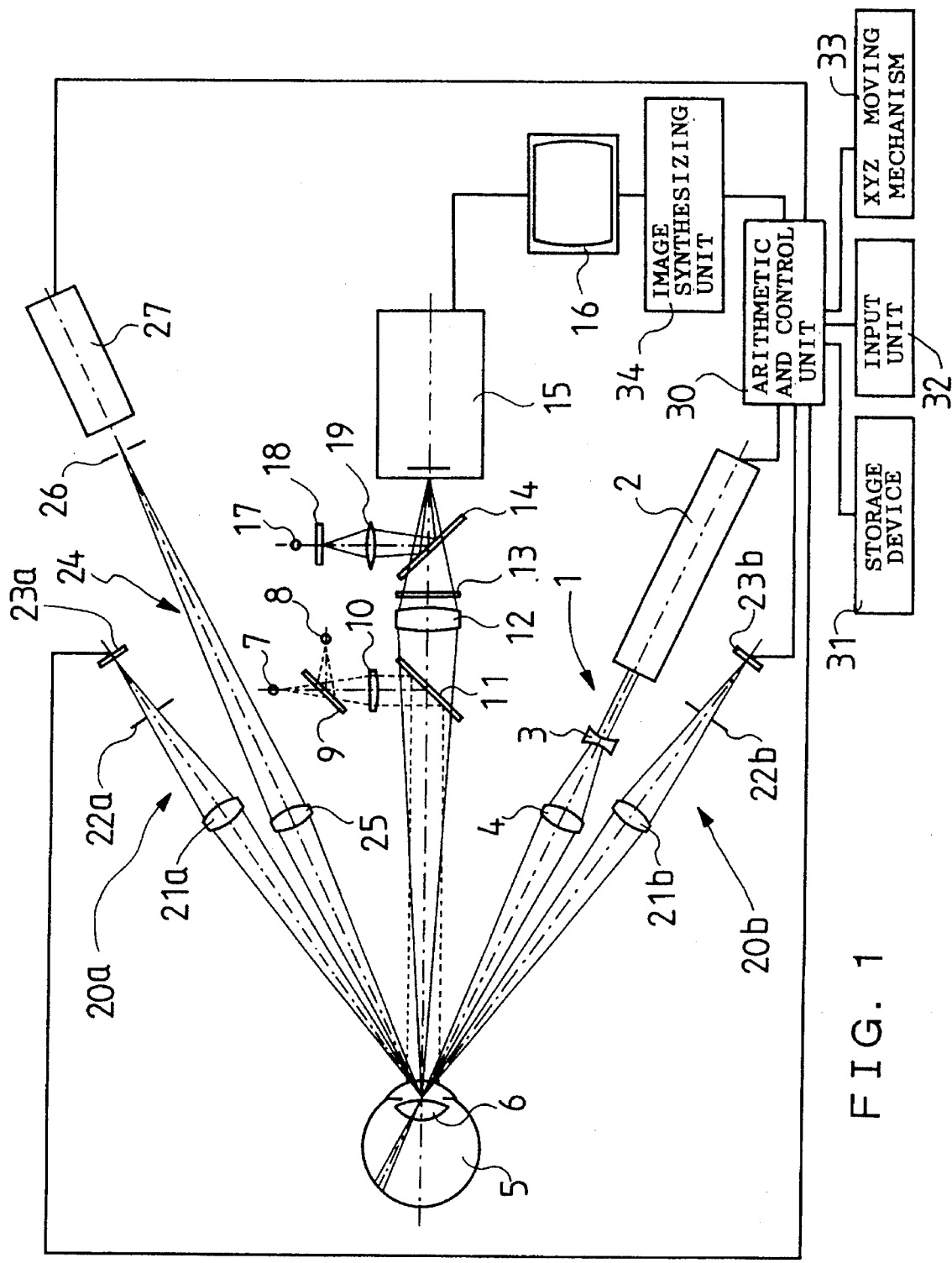
FIG. 1 is a diagrammatic view of an optical system and an electrical system included in an ophthalmometric apparatus in a preferred embodiment according to the present invention.

Referring to FIG. 1, the ophthalmometric apparatus comprises an optical system and an electrical system.

Optical System

The optical system comprises a laser light projecting optical system 1, a fixation/alignment light projecting optical system, an observation optical system, a reticle projecting optical system, an alignment detecting optical system 20 and a scattered laser light detecting optical system 24.

Laser Light Projecting Optical System

The laser light projecting optical system 1 comprises a laser light source 2 that projects an He—Ne visible laser light toward the examinee's eye 5 a lens 6, an expander lens 3 and a condenser lens 4.

Fixation/Alignment Light Projecting Optical System

The fixation/alignment light projecting optical system comprises an alignment point light source 7 that emits alignment infrared light for alignment, a fixation point light source 8 that emits visible light for fixation, a dichroic mirror 9 that transmits infrared light and reflects visible light, a collimating lens 10 and a beam splitter 11.

An alignment infrared rays emitted by the alignment point light source 7 travel through the dichroic mirror 9. The collimating lens 10 collimates the alignment infrared rays into a parallel infrared beam and the beam splitter 11 reflects the parallel infrared beam toward the examinee's eye 5. The dichroic mirror 9 reflects fixation light rays emitted by the fixation point light source 8 toward the collimating lens 10, the collimating lens 10 collimates the fixation light rays into a parallel fixation light beam, and the beam splitter 11 reflects the fixation light beam toward the examinee's eye 5.

Observation Optical System

Figure 2:
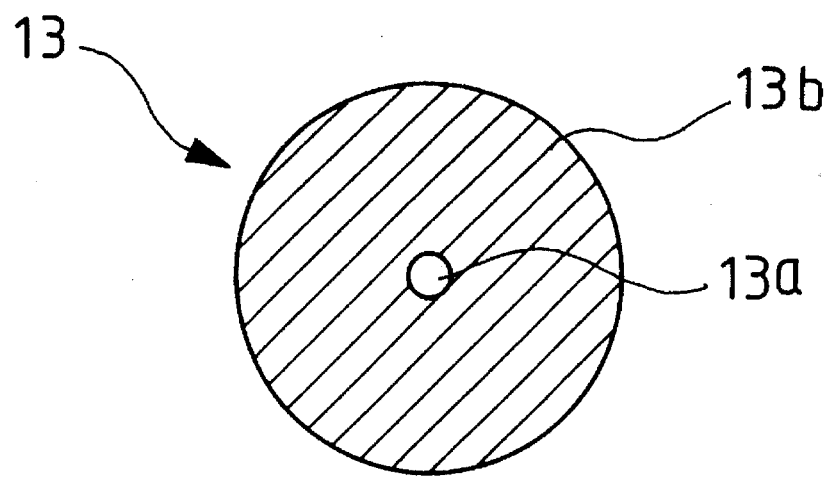
FIG. 2 is a plan view of a filter included in the ophthalmometric apparatus of FIG. 1.

The observation optical system comprises a focusing lens 12, a filter 13, a beam splitter 14, a CCD camera 15 and a TV monitor 16. As shown in FIG. 2, the filter 13 has a central region 13a that transmits visible light and infrared light, and a peripheral region 13b that transmits only the laser light emitted by the laser light source 2 and absorbs light rays other than the laser light. The filtering characteristics of the filter 13 may be embodied by properly coating the substrate or by forming an aperture in the central region 13a of a glass filter that absorbs light rays other than the laser light emitted by the laser light source 2.

The beam splitter 14 aligns the respective optical axes of the reticle projecting optical system and the observation optical system.

Reticle Projecting Optical System

The reticle projecting optical system comprises a reticle projecting light source 17, a reticle 18 provided with a circular mark, not shown, and a projection lens 19. An image of the reticle 18 illuminated with the light emitted by the reticle projecting light source 17 is reflected by the beam splitter 14, the projection lens 19 focuses the image of the reticle 18 on the image sensor of the CCD camera 15, and the TV monitor 16 displays the image of the reticle 18.

Alignment Detecting Optical Systems

The alignment detecting optical system 20 comprises two alignment index detecting optical systems 20a and 20b. The alignment index detecting optical system 20a (20b) comprises a focusing lens 21a (21b), a telecentric aperture 22a (22b) and a two-dimensional image sensor 23a (23b), such as a two-dimensional CCD or a two-dimensional PSD.

Scattered Laser Light Detecting Optical System

The scattered laser light detecting optical system 24 for detecting scattered light scattered by the lens 6 of the examinee's eye 5 comprises a focusing lens 25, an aperture 26 and a light sensor (photomultiplier) 27.

Electrical System

The electrical system comprises an arithmetic and control unit 30, a storage device 31, an input unit 32, an XYZ moving mechanism 33, and an image synthesizing unit 34. The arithmetic and control unit 30 calculates position data representing the positional relation between the ophthalmometric apparatus and the examinee's eye 5 on the basis of the output signals of the two-dimensional image sensors 23a and 23b, and controls the component systems of the ophthalmometric apparatus. The storage device 31 stores the coordinates of the objective part P and the like. The input device 32 is operated to enter identification data including the examinee's identification (ID) number, the date of examination and such. The XYZ moving mechanism 33 drives the optical system in a three-dimensional space relative to the examinee's eye 5.

In operation, the examinee's eye 5 is located at a predetermined position, and then the alignment point light source 7 and the reticle projecting light source 17 are turned on. An image of the front of the examinee's eye 5 illuminated with near-infrared light emitted by an illuminating light source, not shown, and a reticle image of the reticle 18 projected by the reticle projecting optical system are received by the CCD camera 15 and are displayed on the screen of the TV monitor 16.

The light rays emitted by the alignment point light source 7 and the fixation point light source 8 travel through the dichroic mirror 9, the collimating lens 10 and the beam splitter 11 and fall on the examinee's eye 5. The examinee is required to fix the examinee's eye 5 on the fixation lamp. The reflected alignment light rays reflected by the surface of the cornea are received by the observation optical system and the alignment detecting optical system 20.

Figure 3:
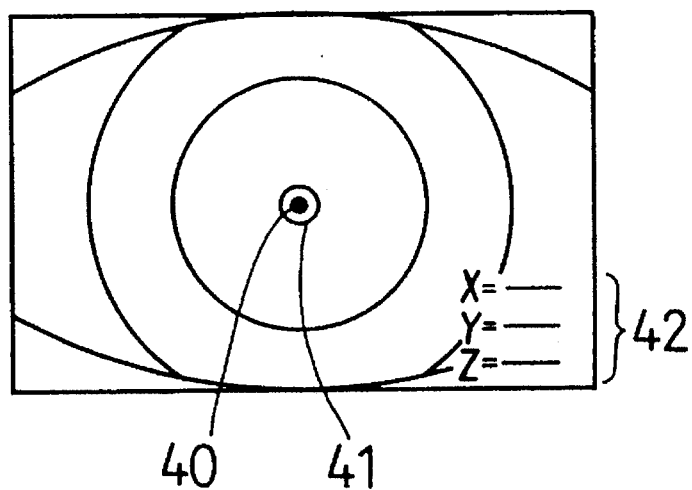
FIG. 3 is a pictorial view of a screen of a display displaying coordinate data.

In the observation optical system, the beam splitter 11 transmits the alignment light rays, the focusing lens 12 focuses the alignment light rays, and only the alignment light lays passed through the central region 13a of the filter 13 is focused in a bright spot on the photosensor of the CCD camera 15. The bright spot of the alignment light rays is superposed on the reticle image on the screen of the TV monitor 16. The XYZ move key of the input unit 32 is operated to control the XYZ moving mechanism 33 to move the optical system vertically and horizontally relative to the examinee's eye 5 so that the bright spot coincides with the center of the reticle image. The optical system may be moved for XYZ positioning by operating the joystick of the ophthalmometric apparatus. When the bright spot of the alignment light rays is aligned with the center of the reticle image, the alignment light rays are focused in bright spots on the two-dimensional image sensors 23a and 23b of the alignment index detecting optical systems 20a and 20b respectively, and then the two-dimensional image sensors 23a and 23b provides position signals representing the respective positions of the bright spots thereon. The position signals are given, after being processed by a predetermined signal processing process, to the arithmetic and control unit 30. The arithmetic and control unit 30 performs predetermined operations on the input position signals to obtain the coordinates (x, y, z) of the bright spot of the alignment light rays on the examinee's eye 5 with respect to a reference position and the coordinates (x, y, z) are displayed on the screen of the TV monitor 16. A method of obtaining the coordinates is described in detail in U.S. Pat. application Ser. No. 08/297,892 filed on Aug. 30, 1994. FIG. 3 shows a picture displayed on the screen of the TV monitor 16, in which indicated at 40 is the bright spot of the alignment light rays reflected by the cornea, at 41 is the reticle image and at 42 are the coordinates. The examiner operates the XYZ moving mechanism 33 for positioning referring to the image of the front of the examinee's eye 5 and the coordinates 42 so that the bright spot is aligned with the objective part P.

Figure 4:
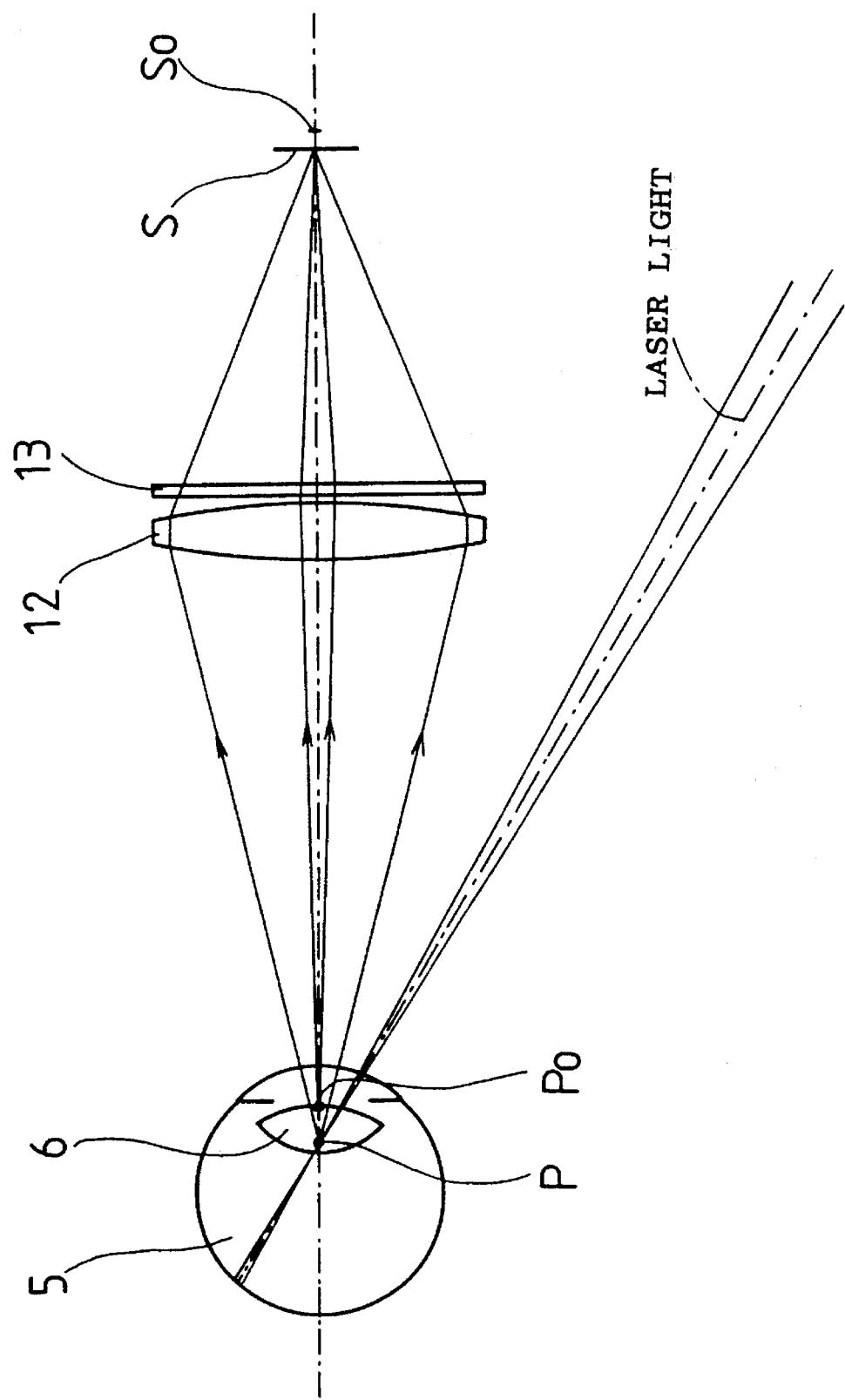
FIG. 4 is a diagrammatic view of assistance in explaining the relation between the corneal reflection of alignment light rays filtered by the filter and laser light projected on an objective part in the examinee's eye.

After the bright spot has been aligned with the objective part P, the laser light source 2 is turned on to project laser light on the examinee's eye 5. The objective part P can be observed through the observation optical system regardless of the axial position of the objective part P in the examinee's eye 5. As shown in FIG. 4, the alignment light rays reflected by the cornea travels through the observation optical system as if they were emitted from a corneal point P0 of reflection. Part of the reflected alignment light rays reflected by the cornea is absorbed by the peripheral region 13b of the filter 13, which absorbs light rays other than the laser light, and only a thin beam of the alignment light rays passes through the central region 13a. Therefore, the observation optical system has a large depth of focus. Accordingly, the bright spot of the alignment light rays focused on the surface S of the image sensor is not blurred significantly even if the optical system is aligned with the objective part P axially apart from the corneal point P0 of reflection, so that satisfactory observation of the objective part P is possible. Since the peripheral region 13b transmits the laser light projected by the laser light projecting optical system 1 on the objective part P in the examinee's eye 5 and reflected by the objective part P, a bright image of the objective part P can be formed for observation.

The scattered laser light emitted by the laser light source 2 and scattered by the objective part P is focused by the focusing lens 25 of the scattered laser light detecting optical system 24 on the aperture 26 for limiting the measuring region. The light sensor 27 disposed behind the aperture 26 detects the scattered laser light. The arithmetic and control unit 30 analyzes the intensity of the scattered laser light detected by the light sensor 27 to determine the opacity of the objective part P. The measured result is given through the image synthesizing unit 34 to the TV monitor 16 to display the same on the screen of the TV monitor 16 and is stored in the storage device 31. The coordinates of the objective part P when a trigger signal for triggering a laser light emitting operation, the examinee's ID number, the date of measurement and such are stored in the storage device 31.

The optical system can automatically be aligned with the examinee's eye by specifying the coordinates of the objective part measured and stored in the storage device 31 on the preceding date of examination by entering the examinee's ID number and necessary information by operating the input device 32 or by directly entering the coordinates by operating the input device 32 before measuring the same examinee's eye again. The arithmetic and control unit 30 reads the previously stored coordinates of the objective part from the storage device 31, compares the coordinates of the present position of the objective part with the coordinates read from the storage device 31 to determine the dislocation of the present position from the position represented by the coordinates read form the storage device 31. Then, the arithmetic and control unit 30 controls the servomechanism of the XYZ moving mechanism 33 on the basis of the dislocation to align the optical system automatically with the objective part.

Figure 5:
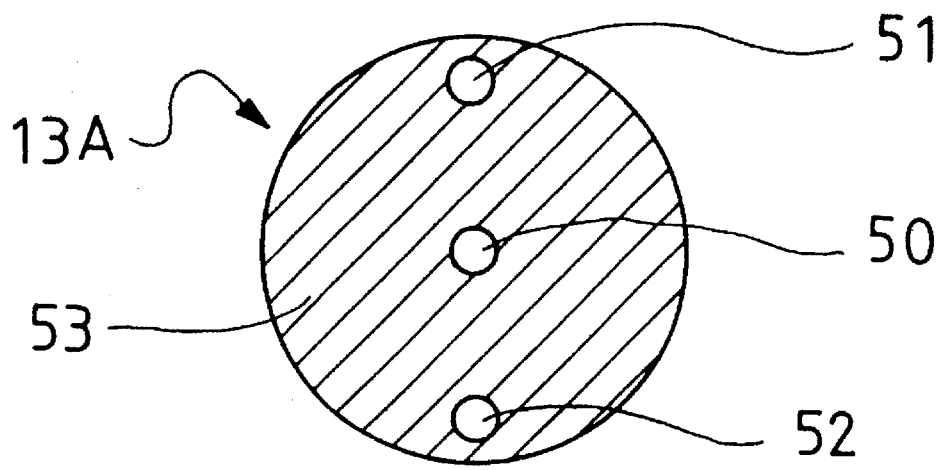
FIGS. 5(a), 5(b), and 5(c) are plan view of other filters suitable for use in the present invention.
Figure 5:
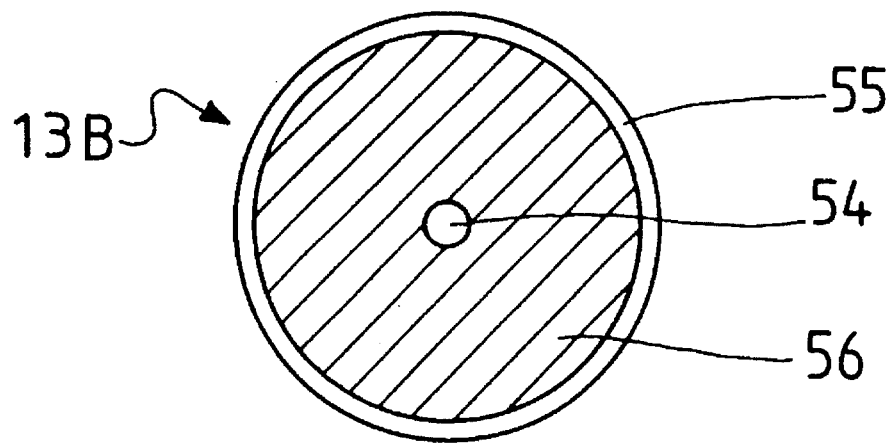
Figure 5C:
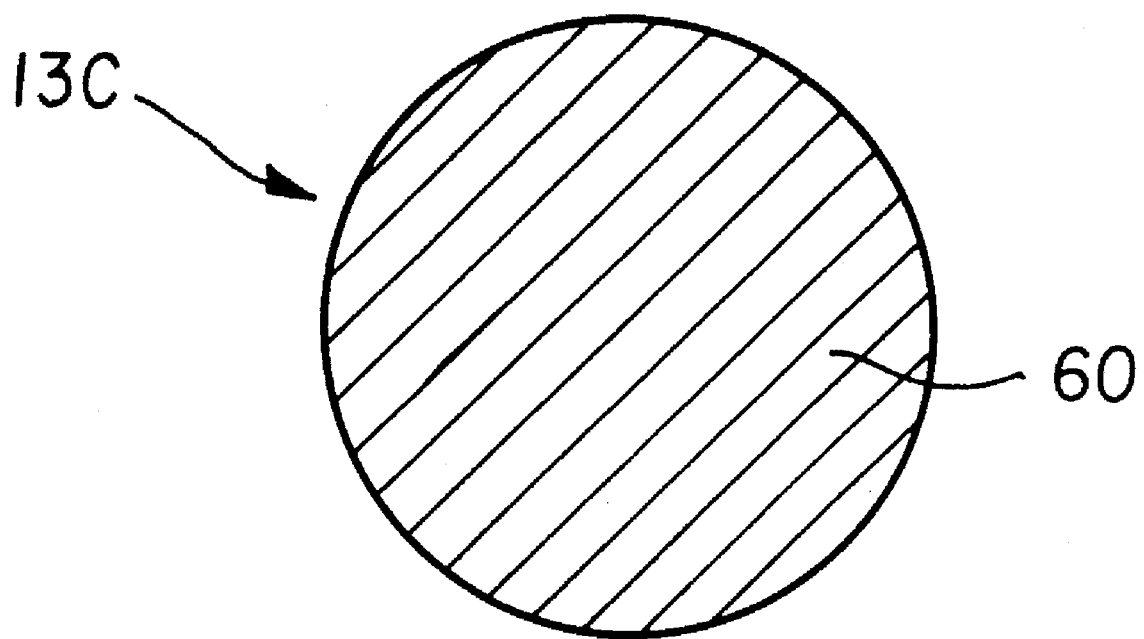

The bright spot of the alignment light rays displayed on the screen of the TV monitor 16 of the observation optical system is small, and the conjugate position to the position of the bright spot of the corneal reflection cannot visually be recognized (a position whose z-coordinate displayed on the screen of the TV monitor 16 is zero is the conjugate position). However, the focus can be confirmed when a filter 13A shown in FIG. 5(a) or a filter 13B shown in FIG. 5(b) is employed. The filter 13A is provided with a central aperture 50 and peripheral apertures 51 and 52 to pass the alignment light rays, and a shaded region 53 that absorbs the alignment light rays. The filter 13B is provided with a central region 54 and a peripheral region 55 to pass the alignment light rays, and a shaded region 56 that absorbs the alignment light rays. The alignment light rays reflected by the cornea toward the observation optical system may be intercepted before the alignment light rays fall on the image sensor of the CCD camera 15, and a bright spot may be formed electrically and displayed on the screen of the TV monitor 16 at a position determined on the basis of position data provided by the alignment detecting optical system 20 FIG. 5(c) shows filter 13(c) including shaded region 60 that absorbs the alignment light rays, thereby intercepting the alignment light rays before they fall on the image sensor of the CCD camera 15. The electrically formed bright spot can readily be removed if the bright spot is a hindrance to the observation of the front of the examinee's eye 5.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. An ophthalmometric apparatus having a measuring system to be positioned relative to an objective part in the examinee's eye, said measuring system including a measuring light rays projecting system for protecting measuring light rays into an examinee's eye, comprising:

an alignment light projecting system for projecting alignment light rays on the examinee's eye;

a position detection optical system for detecting the position of a bright spot of a corneal reflection formed by the alignment light projecting system;

a position calculating means for calculating position data representing the position of the examinee's eye relative to the reference position of the ophthalmometric apparatus on the basis of detection data provided by the position detecting optical system; and an observation optical system for observing the front of the examinee's eye, including an optical element which intercepts a part of the alignment light rays reflected by the cornea, and transmits the observing light rays from the front of the examinee's eye.

2. An ophthalmometric apparatus according to claim 1, wherein the ophthalmometric apparatus further comprises a display means for displaying position data representing the position of the examinee's eye, calculated by the position calculating means.

3. An ophthalmometric apparatus according to claim 2, wherein the observation optical system has a display means for displaying position data representing the position of the examinee's eye, calculated by the position calculating means, and wherein the optical element intercepts the alignment light rays reflected by the cornea completely.

4. An ophthalmometric apparatus according to claim 1, wherein the ophthalmometric apparatus further comprises;
   a storage means for storing the position data representing the position of the examinee's eye, calculated by the position calculating means; and
   a deviation calculating means for reading the position data from the storage means, and comparing the position data read from the storage means and position data representing the existing position of the examinee's eye calculated by the position calculating means, to determine the deviation of the existing position from the position represented by the position data read from the storage means.

5. An ophthalmometric apparatus according to claim 4, wherein the ophthalmometric apparatus further comprises a display means for displaying the deviation calculated by the deviation calculating means.

6. An ophthalmometric apparatus according to claim 4, wherein the ophthalmometric apparatus further comprises a driving means for driving the measuring system for movement according to the deviation calculated by the deviation calculating means.

7. An ophthalmometric apparatus according to claim 1, wherein the position detecting optical system comprises two alignment index detecting optical systems for detecting the bright spot of corneal reflection from two different directions respectively.

8. An ophthalmometric apparatus according to claim 1, wherein the optical element has a central region that transmits the alignment light rays.

9. An ophthalmometric apparatus having a measuring system, said measuring system including a measuring light rays protecting system for protecting measuring light rays into an examinee's eye, comprising:

an observation optical system for observing the front of an examinee's eye;

an alignment light projecting system for projecting alignment light rays toward the examinee's eye;

an alignment detecting optical system for detecting the position of a bright spot of corneal reflection formed by the alignment light projecting optical system;

an arithmetic means that calculates the positional relation of the examinee's eye with the ophthalmometric apparatus on the basis of detection data provided by the alignment detecting optical system; and a filter disposed in the observation optical system having a central region on the optical axis of the observation optical system, wherein the central region transmits the alignment light rays, and a peripheral region of the filter transmits the measuring light rays and observing light rays;

the ophthalmometric apparatus being moved relative to the examinee's eye according to data provided by the arithmetic means.

10. An ophthalmometric according to claim 9, wherein the filter has a further peripheral small region which transmits the alignment rays.

11. An ophthalmometric apparatus according to claim 9, wherein the filter has a region along its periphery that transmits the alignment light rays.

12. An ophthalmometric apparatus according to claim 9, wherein the ophthalmometric apparatus further comprises a display means for displaying the data provided by the arithmetic means.

13. An ophthalmometric apparatus according to claim 9, wherein the ophthalmometric apparatus is an apparatus for measuring the opacity of the lens of the examinee's eye.

\* \* \* \* \*